United States Patent [19]

Redner

[11] Patent Number: 4,668,086
[45] Date of Patent: May 26, 1987

[54] STRESS AND STRAIN MEASURING APPARATUS AND METHOD

[76] Inventor: Salomon Redner, 21 Terrace Rd., Norristown, Pa. 19401

[21] Appl. No.: 736,175

[22] Filed: May 20, 1985

[51] Int. Cl.[4] ............................................. G01B 11/18
[52] U.S. Cl. ...................................... 356/33; 356/327
[58] Field of Search ................... 356/367, 33, 35, 327

[56] References Cited

U.S. PATENT DOCUMENTS 3,443,090  5/1969  Sundstrom ...................... 356/327 X
3,481,671 12/1969  West et al. .......................... 356/327

OTHER PUBLICATIONS

Redner, "New Automatic Polariscope System", *Exptl. Mech.*, vol. 14, No. 12, pp. 486–491, 12/74.

*Primary Examiner*—Davis L. Willis
*Assistant Examiner*—Matthew W. Koren
*Attorney, Agent, or Firm*—Ferrill and Logan

[57] ABSTRACT

Relative retardation resulting from passage of polarized white light through a stressed transparent material is measured automatically, by dividing the emerging polychromatic light into plurality of component beams, each containing one wavelength (or color) only, transforming the light intensity carried by each component beam into an electrical signal, and using these electrical signals to measure the relative retardation, proportional to the stress in the transparent material.

Means are provided to compare the spectral distribution of the light intensity measured at several wavelengths to the calculated distribution using an assumed value of retardation. Iterative (repetitious) calculations are performed until the measured distribution and calculated, using assumed retardation, agree. The retardation yielding agreement with the measured distribution is the measured retardation reflecting the stress in the material.

10 Claims, 8 Drawing Figures

STRESS AND STRAIN MEASURING APPARATUS AND METHOD

BACKGROUND OF THE INVENTION a. Field of the Invention

The present invention relates to apparatus for measuring birefringence of stressed material automatically, and especially to apparatus capable of making plural measurements of birefringence without requiring the specialized skill of one trained in the art of photoelasticity.

b. Description of the Prior Art

Photoelasticity is the property exhibited by some transparent isotropic solids of becoming doubly refracting when subjected to stress and is used in experimental stress analysis. Since differences of principal stress can be established at every point in transparent solids using photoelasticity techniques, such techniques have become increasingly useful for establishing design criteria, improving product integrity and reliability, verifying designs for structural safety, and reducing product weight and costs.

It is known that the index of refraction (n) for a transparent homogeneous isotropic material, is equal to the speed of light in a vacuum (c) divided by the speed of light in the transparent homogenous isotropic material (v). For such a material the index of refraction is independent of the orientation of any plane of polarized light being transmitted through the transparent material. Although the transparent material, and notably plastics, are isotropic when unstressed, they become anisotropic when subjected to stress or deformation. The index of refraction thus becomes a function of the intensity of stresses applied and the direction of these stresses.

Originally, photoelasticity was employed as a tool for the analysis of flat models being subjected to a plane stress. In this simplified form it provided information on stress concentration factors for typical discontinuities, such as holes, notches, and grooves. Much of this information has been compiled in handbooks and design manuals.

A process of "stress freezing" was developed, in which a three-dimensional model of a structure is: (1) cast or machined utilizing a stress free transparent plastic, (2) heated to its softening point, and (3) finally subjected to forces, pressures and other moments such that upon cooling the completed model the pattern of birefringence and deformation is locked in. A model obtained by stress freezing can be sliced into any number of desired planes and every plane can then be analyzed using photoelasticity so as to provide complete three-dimensional stress analysis of the model.

More recently, techniques for testing the structures have been developed whereby transparent materials (or coatings) are cemented to a structure and surface stresses are measured using a reflection photoelasticity technique.

Several techniques have been employed to measure birefringence. Normally, polariscopes have been employed to effect such measurements by measuring at each point both the direction and magnitude of the difference of principal stresses or strains.

A transmission polariscope is used to analyze transparent models or specimens and is also used for the analysis of sliced planes or three-dimensional models. It has a light source and a polarizer which is positioned on one side of a model or specimen to be analyzed, and an analyzer which is positioned on another side of the model.

A reflection polariscope, which employs the principle of double passage of light, is used mainly for photoelastic coatings, with polarizer and analyzer placed on the same side of the model material.

These polariscopes can either be "plane" or "circular". In each of the two polariscope arrangements, plane and circular, intensity of light transmitted (I) is a function of the relative retardation ($\Delta$) and the orientation of principal stresses ($\beta$).

The relations between the transmitted light intensity (I), relative retardation, ($\Delta$) orientations ($\beta$) and principal stresses ($\delta 1$, $\delta 2$) are well known.

For the plane polariscope:

$$I = Io(\sin^2 \cdot 2\beta)\left(\sin^2 \frac{\pi\Delta}{\lambda}\right)$$

For circular polariscope, using crossed polarizers (also called "darkfield"):

$$I = Io \sin^2 (\pi\Delta/\lambda)$$

For circular polariscope, using parallel polarizers (also called ("light field"):

$$I = Io \cos^2 (\pi\Delta/\lambda)$$

In these expressions:
I and IO is the emerging and entering light intensity.
$\lambda$ is the wavelength of monochromatic light.
B is the direction of principal stresses.

The difference of principal stresses ($\delta 1 - \delta 2$) is given by Brewster's law:

$$\delta 1 - \delta 2 = (\Delta/tc)$$

where (t) is the thickness of stressed material and (c) is the material sensitivity.

In the plane polariscope, the intensity of light transmitted becomes zero if the polarizer is parallel to one of the directions of principal stress ($\delta 1$, $\delta 2$). This condition is satisfied at several points, normally, and a line or a complete area will appear black. Such a line or an area is called an isoclinic line. At every point on an isoclinic line, the direction of principal stress is either the same as the direction of the polarizer, or perpendicular to it. When the polarizer and analyzer are rotated together, the isoclinic line moves to a new position, thus making it possible to completely explore directions of principal stress throughout the part analyzed.

The circular polariscope is similar to the plane polariscope except that it additionally includes a pair of quarter wave plates. The purpose of the quarter wave plates is to eliminate sensitivity of the polariscope to the direction of principal stresses. In the case of the circular polariscope, where the analyzer is perpendicular to the polarizer (dark field), light intensity becomes zero when the relative retardation is equal to an integral multiple of the wave length of light used ($\Delta = N\lambda$). If monochromatic light is used, a series of black lines are observed. Along every black line, i.e. isochromatic fringe, the "fringe order" (N) remains constant (N=0, 1, 2, ... ). Strain and stress fringe values ($C_\epsilon, C_E$) are usually established by calibration. The difference of principal stresses or principal strains can be established at every point once the fringe order (N) is measured.

One of the difficulties in using polariscopes has been the skill required and human evaluation necessary to determine the fringe order (N) both integers and fractions.

In order to accomplish this, a compensator, such as a quartz crystal, or permanently deformed plastic exhibiting a calibrated variable retardation, is introduced according to one technique between the specimen analyzed and the analyzer. The compensator is superimposed so that its principal directions coincide with the directions of principal stresses in the plastic specimen plate. When retardation in the compensator and the measured retardation are numerically equal, but opposite in sign, total intensity observed is zero.

One apparatus, U.S. Pat. No. 3,902,805, addresses the measurements of relative retardation of light waves propagating at different speeds through a stressed material automatically by splitting light waves emerging from the stressed plate or coating into at least two beams, filtering each beam with a filter which transmits a different wave length, transforming the light intensity from each filter into electric signals, and measuring phase shift between those electrical signals resulting from rotation of a polarizer by means of a motor, the difference in phase between the signals is proportional to retardation and the birefringence. The resulting phase difference can be displayed on a voltmeter, or a digital meter, or can be continuously recorded. The above measurement can be accomplished only after the direction of the measured stresses is determined and the quarter wave plate is then placed in alignment with the direction of stress.

From the above discussion it can be seen that the measuring of birefringence ($\Delta/t$) has been accomplished by one of the following methods:

(1) Full field isochromatic photography, revealing pictorially a complete stress distribution;
(2) Point-per-point use of a Babinet-type compensator;
(3) Point-per-point measurements of fractional orders, using the analyzer rotation; and
(4) Automatic, point-per-point electronic data acquisition systems, using one of the above listed principles. (See U.S. Pat. No. 3,902,805).

In all above methods difficulties arise because before the actual value of the retardation can be established, the direction of stresses must be determined, a proper numerical value must be assigned to each fringe observed, and when the points of interest are not covered by a fringe, a "fractional" order must be measured.

SUMMARY OF THE INVENTION

An object of the present invention is to provide apparatus capable of determining birefringence and retardation or another event related to these qualities.

Another object of the present invention is to provide apparatus for determining fringe orders.

A further object of the present invention is to provide apparatus for automatically measuring stress in transparent materials by means of birefringence and retardation quantities without first determining the direction of stress.

Yet another object of the present invention is to provide apparatus which is capable of measuring birefringence automatically even when retardation is many times larger than the wave length employed without the need of measuring the direction of stress.

Accordingly, there is provided an apparatus for the analysis of stress and strain in transparent members having a polychromatic light source; a polarizer arranged to intercept the light provided by the source so as to pass polarized light through at least a portion of the transparent member on which birefringence is to be measured; an analyzer positioned to receive the light emanating from the member comprising a second polarizer; quarter wave plates adjacent to the polarizer and analyzer permitting the circular polarizer operation set up; a device for splitting the emerging polarized beam into a plurality of component beams each containing a different wave length; a plurality of optical detectors arrayed to receive the differing beams within a discrete frequency range for each detector, whereby each detector transforms the component beam received into electrical signals; a circuit to adjust gain on each detector so as to maintain their signal outputs at substantial levels; a recording component receiving the signal values corresponding to the intensity of each detected beam component; a computer receiving values representative of the measured light intensities at different wave lengths and programmed to calculate the retardation from these measured light intensities.

Several algorithms are possible for the programming; the simplest approach, known as a "best fit" concept, consists of calculating the light intensity for each component beam using an assumed value of retardation, comparing the calculated intensities to the measured intensities, taking note of the discrepancies, and then testing another assumed value; until the discrepancy between the calculated set and the measured values are minimized. The assumed value for retardation which solves the system of equations therefore becomes the measured retardation in the transparent member 17a (or 17b).

By measuring the light intensity of a plurality of preselected colors, i.e. to obtain data samples, then solving the known photoelasticity curve for the retardation quantity using these data samples, retardation is obtained without the need to first determine stress orientation, i.e. direction of stress.

DESCRIPTION OF THE DRAWINGS

The structure, operation, advantages and features of the invention will be apparent to those skilled in the art from the following detailed description read in conjunction with the accompanying drawings, in which like numerals refer to like elements and in which.

DETAILED DESCRIPTION OF THE INVENTION a. Prior Art

Figure 1:
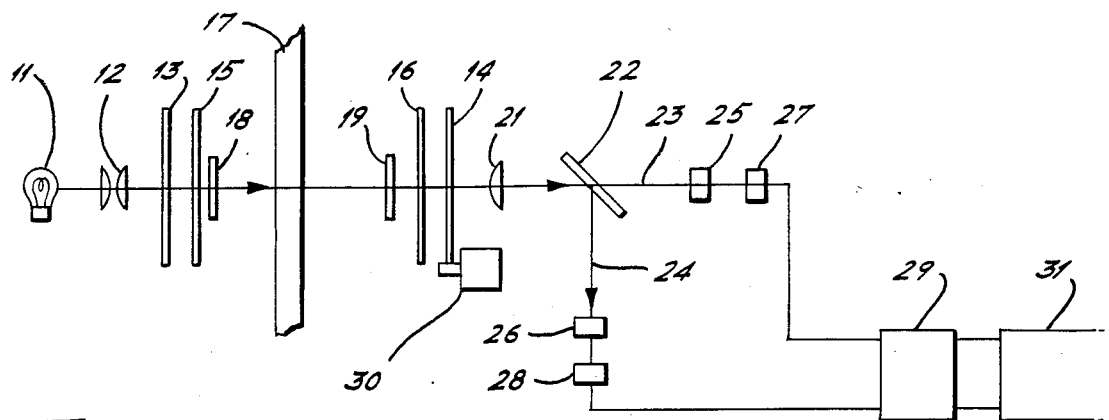
FIG. 1 is a schematic illustration of a prior art light transmission apparatus for automatically determining the birefringence of a stressed member.

FIG. 1 illustrates a prior art apparatus for automatically measuring birefringence, without intervention of the human eye, and without requiring special skill of an operator to recognize or count fringe orders. A suitable light source, such as an incandescent light 11, for producing a polychromatic light is employed. An arrangement of one or more lenses 12 can be incorporated in the system in order to make the most efficient use of the illumination from light source 11. Light propogates through the polariscope consisting of polarizers 13 and 14. The polariscope also contains quarter wave plates 15, 16. Light is passed through the model members of specimen 17 under investigation. The elements 13, 14, 15, 16 of the polariscope are mounted on opposite sides of the member 17, as shown.

In either reflection or transmission modes, additional birefringent plates 18 and compensators 19 can be incorporated into the system.

Light transmitted through polarizer 14 passes through a suitable lens arrangement 21, directing the propogated light to a beam splitter, or partial mirror 22, which divides the light into at least two beams 23, 24. A filter 25 which transmits light of one wave length ($\lambda 1$), is placed in the path of beam 23, while another filter 26, which transmits light of another wave length ($\lambda 2$), is placed in the path of beam 24. Photoelectric devices 27 and 28 receive the filtered beams 23 and 24, respectively. These photoelectric devices 27, 28 can be of any suitable form, such as photoresistive cells, which change their resistance as function of light intensity; a photovoltaic cell, which generates a voltage upon illumination; or photomultipliers, manufactured in various configurations, which provides electrical output.

Regardless of the nature of the photoelectric devices used, phase meter 29 is provided with two electrical signals, one relating to the light intensity of beam 23 and the other to the light intensity of beam 24.

A motor 30 is used to achieve modulation of the light intensity emerging from an investigated point. Electric motor 30 causes polarizer 14 to rotate, at a frequency $\omega$.

In the operation of the described apparatus (FIG. 1), rotation of polarizer 14 causes the modulation of the light intensity emerging from an investigated point. The light intensity of the beams 23 and 24 for time T become:

$$\text{Beam 23: } I\sin^2\left[\omega T - \frac{\pi t c}{\lambda_1}(\delta_1 - \delta_2)\right]$$

$$\text{Beam 24: } I\sin^2\left[\omega T - \frac{\pi t c}{\lambda_2}(\delta_1 - \delta_2)\right]$$

and the photoelectric devices 27 and 28 provide electric signals proportional to those light intesities. These signals, which are not necessarily of the same amplitude, exhibit a difference in phase P proportional to the retardation ($\Delta$). This difference in phase which can be expressed as $$P = \pi t(\delta_1 - \delta_2)\left(\frac{c}{\lambda_1} - \frac{c}{\lambda_2}\right)$$

can be measured easily using phase meter 29. The result of the phase measurement can then be displayed on a suitable device 31, and/or continuously recorded using an oscillograph.

b. Method

The method of the present invention is a point-per-point method; however, it offers several simplifications and, therefore, improvement over the prior art. The value of birefringence can be measured without prior knowledge of the direction of principal stress/strain. Because of its simplicity, the optical and electronic means are greatly reduced, and also the human judgment factor and possible resultant error eliminated. Unlike the other automated methods that are inherently slow, the method performed by the apparatus of the present invention acquires data instantaneously, and it can follow the high speed events encountered in dynamic stress analysis.

In a polariscope equipped with quarter-wave plates, the transmitted light intensity (I) can be expressed as:

$$I = I_o \sin^2(\pi\Delta/\lambda) \text{ (dark field)}$$

or $$I = I_o \cos^2(\pi\Delta/\lambda) \text{ (light field)}$$

where ($I_o$) is the entering light intensity ($\Delta$) is the measured retardation and ($\lambda$) is the wavelength of light.

To properly analyze the light intensity emerging from the polariscope, it must be noted that the light intensity emerging from the source S has a well defined spectral content depending upon the filament temperature, and can be expressed as a function of wavelength:

$$I = I_S(\lambda)$$

The transmittance of all the transparent elements (lenses, various filters, windows . . . ) is also a function of wavelength, and can be described as ($T_L$).

The transmittance ($T_M$) of the stressed member is expressed by the equation:

$$T_M = \sin^2(\pi\Delta/\lambda) \text{ (Dark Field)}$$

and $$T_M = \cos^2(\pi\Delta/\lambda) \text{ (Light Field)}$$

The light intensity emerging from the polariscope, and measured by means of properly calibrated detectors, becomes:

$$I = I_o \sin^2(\pi\Delta/\lambda) = I_S \cdot T_L \cdot T_M$$

where $I_S$ is light intensity and $T_L$ is transmittance of the lenses. The electric current output, ($i\lambda$) from the detector-amplifier system becomes:

$$i_\lambda = D \cdot I_S \cdot T_L \cdot T_M$$

and substituting for ($T_M$) its value in the equation above, yields:

$$i_\lambda = D \cdot I_S \cdot T_L \cdot \sin^2(\pi\Delta/\lambda) \text{ (Dark Field)}$$

$$i_\lambda = D \cdot I_S \cdot T_L \cdot \cos^2(\pi\Delta/\lambda) \text{ (Light Field)}$$

where D is the energy conversion (or sensitivity) factor of the photoelectric detector receiving the light emerging from a point.

The photoelastic member under study behaves essentially as a variable-transmittance filter, with the stress at a point acting as a parameter modifying the spectral transmittance ($T_M$).

To calibrate the system, a stress-free transparent material is introduced in a "Light-field" polariscope. The mesured current is:

$$i_\lambda = D \cdot I_S \cdot T_I = S_\lambda$$

and the equations are reduced to:

$$i = S_\lambda \cdot \sin^2(\pi\Delta/\lambda) \text{ (Dark Field)}$$

and $$i = S_\lambda \cdot \cos^2(\pi\Delta/\lambda) \text{ (Light Field)}$$

For each beam of wavelength ($\lambda i$) the transmittance can now be expressed as:

$$T_M = \sin^2\frac{\pi\Delta}{\lambda_i} = \frac{i\lambda_i}{S}$$

where
- (S) are known calibration factors
- ($\lambda i$) are wavelengths of component beams
- ($i_{\lambda i}$) are currents produced by photodetectors and
- ($\Delta$) is the retardation that is measured.

Several values of ($i_{\lambda i}$) are simultaneously acquired; the measured retardation ($\Delta$) is extracted from simultaneous equations:

$$\sin^2\left(\frac{\pi\Delta}{\lambda_i}\right) - \frac{i\lambda_i}{S_\lambda} = 0$$

These equations are solved expediently by computer.

c. Measuring System

Figure 2:
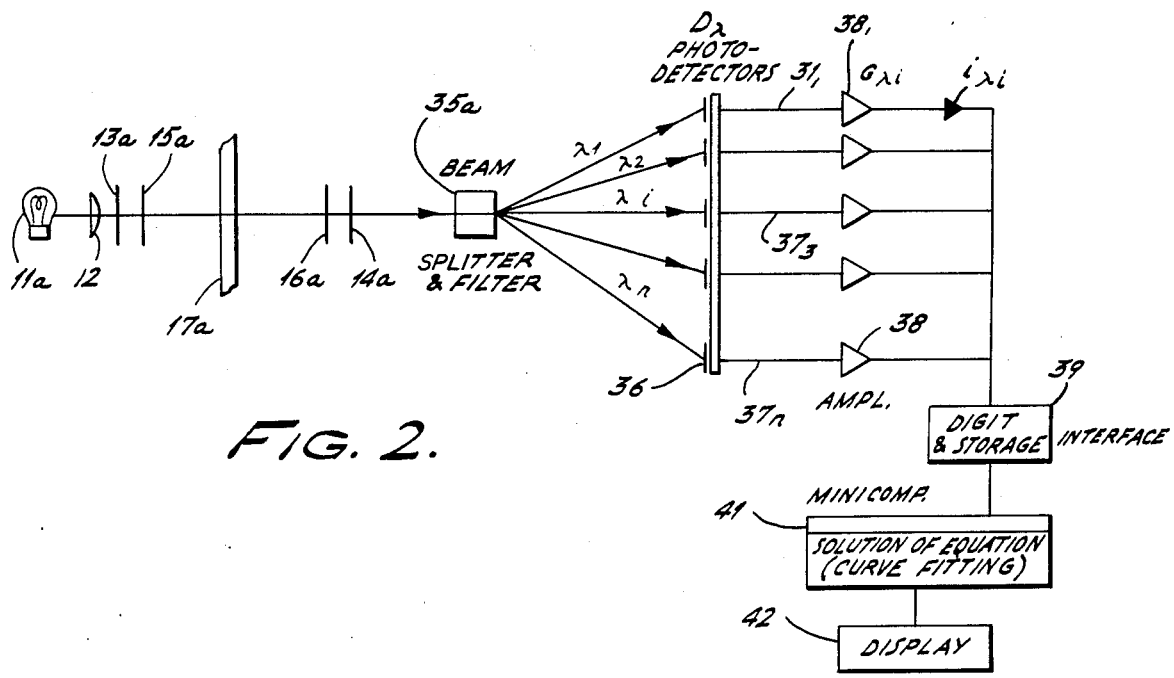
FIG. 2 is a first embodiment of a transmission apparatus for determining stress in a member involving simultaneous spectral data acquisition at several wavelengths, according to the present invention.

Referring now to FIG. 2, a light source 11a, polarizers 13a and 14a, and quarter wave plates 15a and 16a are utilized as in the prior art, FIG. 1, by positioning them about a transparent or translucent member 17a under study. Polarizers 13a and 14a could also be used on the same side of the transparent member 17a, when one of the faces of member 17a reflects light. Instead of a partial mirror acting as a beam splitter, a diffraction grating or a prism 35a, can be employed to accomplish the division of the polarized polychromatic light into plural distinct beams, each carrying a narrow band of wave length, ($\lambda_i$).

Each of the plural beams are projected upon a detector, part of an array of photoelectric detector devices, whereby each detector is dedicated to a respective beam. The detectors 36 can be of commercially avialable photoelectric types. However, there are available for this detector 36 photodiode arrays from E.G.&G. Detector, Incorporated. EGG Specification No. 61200007.

The plural electrical signals ($i_{\lambda i}$) are passed via leads 37 (1) . . . (n) to individual respective amplifiers 38 (1) . . . (n). The gain of these amplifiers 38 can be individually adjusted during the calibration process to optimize the system performance, e.g., to compensate for detector or source characteristics at various wavelengths. Signals from the amplifiers 38 are digitized and stored (along with the gain corrections values) as data in a storage unit 39. The stored or otherwise recorded data is passed to a programmable microprocessor 41, that is programmed to carry out the multiplicity of computations described below until a retardation value is formed which is best fitted to the acquired plural signal values, the retardation numbers being reflective of the stress magnitude in the structure at the load being imposed.

Typically, this minicomputer 41 can be implemented with a Hewlett-Packard Personal Computer Model HP-85 or any similar device.

A typical program stored in the computer memory instructs the calculator to perform a sequence of computations, using the acquired data. One sequence of calculations that can solve the equations shown is:

Select an assumed value of the retardation $X_1$

Calculate the transmittance $\sin^2(\pi X_1/\lambda_i)$ for each wavelength of the array, and the resulting current $i_{\lambda i} = S \cdot \sin^2(\pi X/\lambda_i)$ Establish the discrepancy (i.e. the difference, or error) between the actually measured current and the calculated.

Add the errors for all beams, and retain the result.

Assume a new value of the retardation, $X_2$.

Repeat the steps above. Retain $X_2$ if the error for all beams is smaller than previously computed. Repeating the above procedure, one arrives to an assumed value Xo that yields the light intensities matching exactly the measured values. The Xo is becoming then the solution of the system of equations:

$$\Delta = Xo$$

Figure 3:
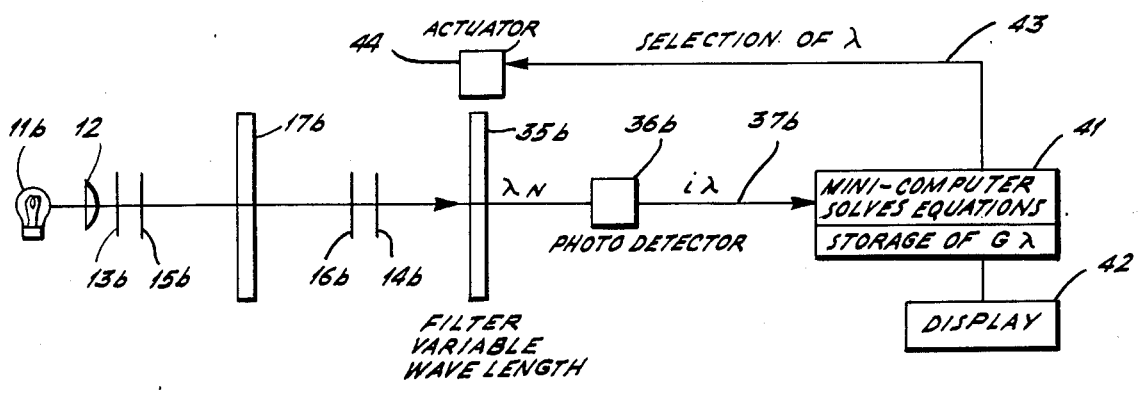
FIG. 3 is an alternate arrangement of a spectral data acquisition system for determining stress in materials by the present invention.

FIG. 3 shows an apparatus where the layout up to but not including the beam divider 35 is identical to that of the embodiment of FIG. 2. A light source 11b, polarizers 13b and 14b and quarter wave plates 15b and 16b are positioned about the stressed model 17b. Thereafter, the polarized, attenuated polychromatic light is passed through a scanning filter 35b, having several variable wavelength bands disposed therein. Any one of several settings on the filter 35b correspond to distinct narrow wavelength bands disposed therein. Any one of several settings on the filter 35b correspond to distinct narrow wavelength bands transmitted. The scanning filter 35b settings may be set manually or by a servo-motor operated gearing device actuator 44, of a commercially available type. This embodiment, while mechanically and electronically simpler than that of FIG. 2, necessarily operates more slowly, and is less advisable for dynamic operations.

The filter 35b transmits successive beams of different wavelengths ($\lambda i$) each of which passes consecutively to single photoelectric device photodetector 36b. Sequentially generated voltages or current ($i_{\lambda i}$) generated by the photodetector 36b are passed via lead 37b directly into the minicomputer 41. The minicomputer 41 is operated to perform the calculation explained above. A feedback signal from computer 41 via lead 43 signals the servo-motor 44 to index the scanning filter 35b to the next wavelength for light transmission.

Figure 4:
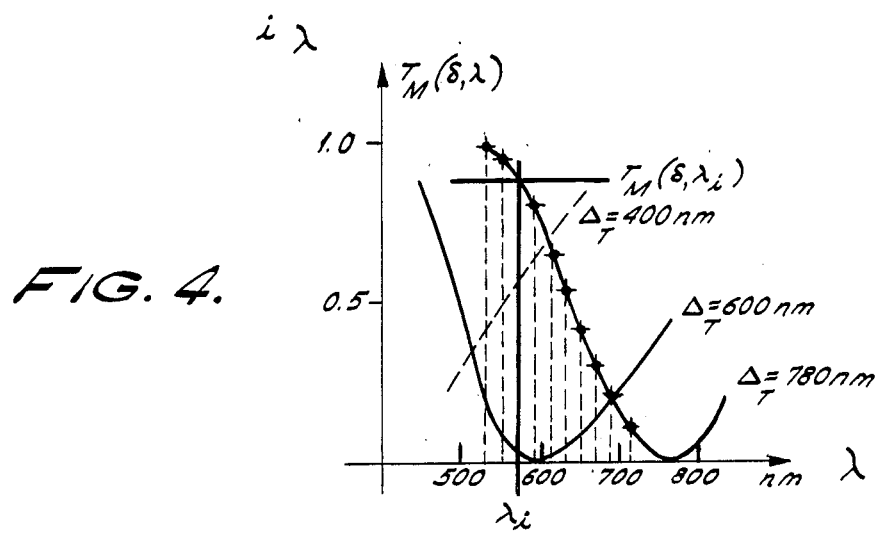
FIG. 4 is a plot of data points, from the scan of a stressed model at several wavelengths, which have been digitized, and which plot is then subjected to "curve fitting" techniques of the present invention.
Figure 5A:
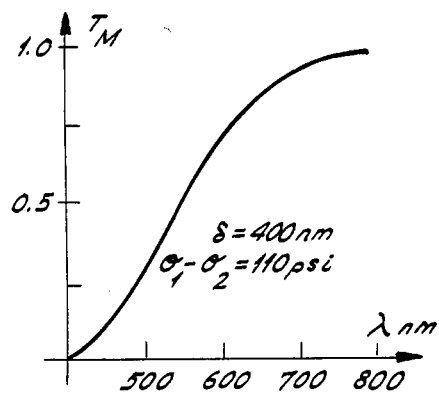
FIGS. 5a–5d depict graphically spectral transmittance pattern curves for a model stressed at four different levels (110, 220, 330, 275 psi.).
Figure 5B:
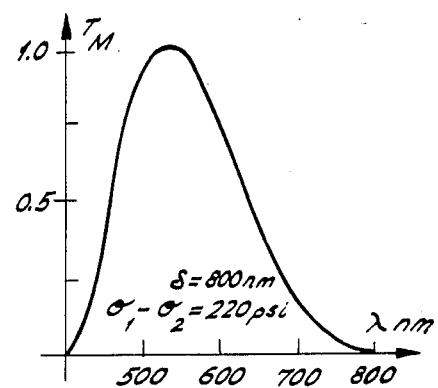
Figure 5C:
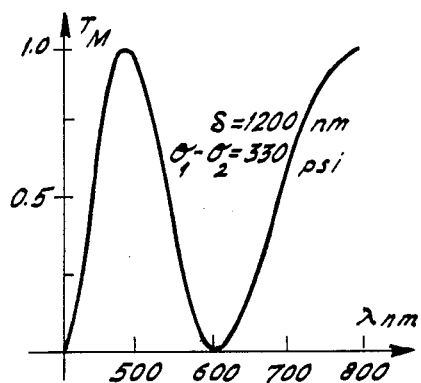
Figure 5D:
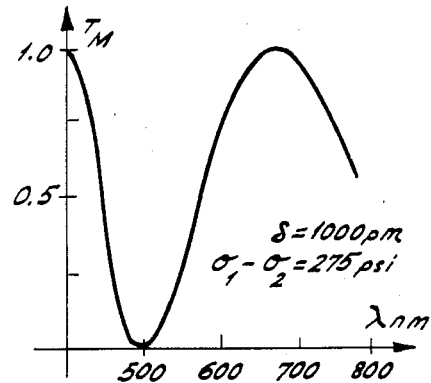

FIG. 4 illustrates a plot scan from a typical stressed member obtained with the invention. The abscissa represents light intensity ($i_{\lambda_i}$), while the ordinate represents wavelengths ranging from 400 to 800 nanometers.

FIGS. 5a–5d graphically illustrate plots of spectral transmittance ($T_M$) for a plastic model, 0.25" thick, subjected to a stress of 110 psi. to 330 psi. provided by the invention. The ordinate is ($T_M$), from 0 to 1.0, and the abscissa is wavelengths, from 400 to 800 nanometers.

The minicomputer 41 was programmed to calculate ($Tm = \text{Sin}^2 (\pi \Delta t/\lambda)$) for several assumed values of ($\Delta_t$) until a value of ($\Delta_t = X_1, X_2 \ldots$) is found that best fits the measured experimental points. Such fit is accomplished when the difference between the calculated ($T_M$) and measured current is minimized by the method of curve fitting. The best fit value of ($\Delta_t$) was then displayed in solving the system of equations, and providing the measured value of stress at a particular point.

The invention, especially as to the embodiment of FIG. 2, measures light intensity ($i_\lambda$) simultaneously at several wavelengths ($\lambda_i$). The information can then be used either for real time analysis and the display of ($\Delta$) or can either be collected and stored with data analysis performed later when computer time is available.

In diagrammatic FIGS. 2 and 3, there is no specific indication of the nature of the medium through which the light rays travel between the indicated elements, there being no indication whether the light is transmitted through air or other gas, or vacuum, or solid material. As will be apparent to those skilled in the art, the intervening spaces through which the light is to travel may be occupied, to whatever extent is desired, by fiber optic elements facilitating the efficient transmission of the light and providing for its conservation, and affording the path flexibility known to characterize use of fiber optics.

From the foregoing, it will be seen that this invention is adapted to obtain all of the ends and objects hereinabove set forth, together with other advantages which are obvious and inherent. The ability to make measurements of retardation without specialized training represents a significant development for expanding the usefulness of photoelasticity as a tool for analysis of stress.

Manifestly, many modifications and variations of the invention as hereinbefore set forth can be made without departing from the spirit and scope thereof and therefore only such limitations should be imposed as are indicated by the appended claims.

What is claimed is:

1. Apparatus for measuring stress and strain induced birefringence in a light transmitting member, comprising:
    a polychromatic light source emanating light;
    a lens to direct said emanated polychromatic light in a beam;
    a polarizer positioned to intercept said light beam and pass said light beam;
    a first quarter-wave birefringent plate arranged to intercept said polarized light beam passed by said polarizer and passing said light beam through at least a portion of said member in which birefringence is to be measured;
    a second quarter-wave birefringent plate arranged to intercept said light beam passed through said member in which birefringence is to be measured;
    an analyzer consisting of a second polarizer adjacent said second quarter-wave birefringent plate and arranged to intercept said light beam passed by said second quarter-wave birefringent plate and pass it on;
    means for splitting the polarized beam passed on by said analyzer into a plurality of component beams each of a different wavelength representative of a specific predetermined color;
    photoelectric detector means positioned to receive each one of said component beams, said detector means providing a distinctive individual electrical signal output representative of each specific predetermined color received;
    means for receiving each detector electrical output signal and for determining the amplitude thereof as representative of the intensity of light color detected and for storing each said intensity value; and
    means for mathematically comparing said stored intensity values in a curve fitting manner against predetermined data for determining the measured retardation, stress and strain magnitude in said member.

2. The apparatus of claim 1 wherein said beam splitting means includes a filter.

3. The apparatus of claim 2 wherein said beam splitting means is a diffraction grating splitting said beam of light into individual component beams each being of a narrow bandwidth.

4. The apparatus of claim 3 also including a plurality of amplifiers each one positioned to receive one of said detector means individual output signals and to said signal amplified to said receiving and determining means.

5. The apparatus of claim 4 wherein said means for mathematically determining stress and strain magnitude includes a computer programmed to solve a system of equations entered thereinto.

6. The apparatus of claim 5 wherein said computer solves said system of equations by an iterative approach.

7. The apparatus of claim 1 wherein said beam splitting means includes an optical splitter simultaneously splitting said light beam into a plurality of component beams and wherein said detector means is an array of individual photo detectors positioned to receive, one each, each of said component beams and for simultaneously each providing an electrical output signal.

8. The apparatus of claim 1 wherein said beam splitting means includes an electrically operated variable wavelength transmitting filter, said variable filter comprising means for changing the selectively transmitted wavelength upon command of control signals obtained from said receiving and determining means, said variable filter being electrically connected to said receiving and determining means.

9. The apparatus of claim 1 wherein said light transmitting member is physically attached to an opaque member wherein stress and strain within said opaque member is transmitted into said light transmitting member.

10. A method of measuring stress magnitude in light transmitting member, comprising the steps of:
    (a) providing a source of polychromatic light;
    (b) focusing said polychromatic light through a first polarization and quarter wave birefringent plate;
    (c) passing said polarized light through said light transmitting member;
    (d) passing said light exiting said transmitting member through a second polarizing and quarter wave birefringent plate;

(e) splitting said light emerging from said second polarizing plate into a plurality of component light beams each of different wave lengths;

(f) detecting each said component light beams and providing an individual electrical signal proportional to said component beam intensity;

(g) electronically storing each electrical signal value as representative of each component beam; and (h) using said stored values to calculate the value of the measured retardation by solving the following equation:

$$I_{\lambda i} = S_\lambda (I i) \sin^2 (\pi X / \lambda i)$$

wherein X is the sought retardation value, $S_\lambda$ is the known calibrating factor, and $\lambda i$ is the wavelength of light, in order to determine the value of retardation in the polarized light passing through the said member.

* * * * *

UNITED STATES PATENT AND TRADEMARK OFFICE
CERTIFICATE OF CORRECTION

PATENT NO. : 4,668,086
DATED : May 26, 1987
INVENTOR(S) : Salomon Redner

It is certified that error appears in the above-identified patent and that said Letters Patent is hereby corrected as shown below:

Column 2, line 67 -- change ($C_E \ C_E$) to ($C_E \ C_f$)

Column 9, line 10 after "of" change ($\Delta_t$) to ($\Delta_t = X_1, X_2 \ldots$)

Column 9, line 11 change ($\Delta_t = X_1, X_2 \ldots$) to ($\Delta_t$)

Signed and Sealed this

Fifteenth Day of September, 1987

*Attest:*

DONALD J. QUIGG

*Attesting Officer*   *Commissioner of Patents and Trademarks*